(12) United States Patent
Park

(10) Patent No.: US 10,178,985 B2
(45) Date of Patent: Jan. 15, 2019

(54) DETACHABLY JOINED ULTRASONIC PROBE DEVICE

(71) Applicant: Humanscan Co., Ltd., Ansan-si, Gyeonggi-do (KR)

(72) Inventor: Wonseop Park, Seoul (KR)

(73) Assignee: HUMANSCAN CO., LTD., Ansan-si, Gyeonggi-do (KR)

( * ) Notice: Subject to any disclaimer, the term of this patent is extended or adjusted under 35 U.S.C. 154(b) by 84 days.

(21) Appl. No.: 14/784,912

(22) PCT Filed: Mar. 21, 2014

(86) PCT No.: PCT/KR2014/002386
§ 371 (c)(1),
(2) Date: Oct. 15, 2015

(87) PCT Pub. No.: WO2014/181961
PCT Pub. Date: Nov. 13, 2014

(65) Prior Publication Data
US 2016/0143618 A1    May 26, 2016

(30) Foreign Application Priority Data

May 9, 2013  (KR) ........................ 10-2013-0052553

(51) Int. Cl.
*A61B 8/14*    (2006.01)
*A61B 8/00*    (2006.01)
(Continued)

(52) U.S. Cl.
CPC .......... *A61B 8/4411* (2013.01); *A61B 8/4444* (2013.01); *A61B 8/4455* (2013.01);
(Continued)

(58) Field of Classification Search
CPC ... A61B 8/4411; A61B 8/4444; A61B 8/4455; A61B 8/4477; A61B 8/4488;
(Continued)

(56) References Cited

U.S. PATENT DOCUMENTS 5,820,549 A    10/1998  Marian, Jr.
5,976,090 A    11/1999  Hanafy et al.
(Continued)

FOREIGN PATENT DOCUMENTS

JP    62195782 U    12/1987
JP    2008289599 A    12/2008
(Continued)

OTHER PUBLICATIONS

European Search Report dated Nov. 30, 2016 in connection with the counterpart European Patent Application No. 14794112.4.
(Continued)

*Primary Examiner* — Mark Remaly
(74) *Attorney, Agent, or Firm* — Hauptman Ham, LLP

(57) ABSTRACT

The present invention relates to a detachably joined ultrasonic probe device, including modular ultrasonic probe and a case for detachably joining with the modular ultrasonic probes, which enables the user to select a suitable ultrasonic probe according to desired performance and diagnosis frequency region. The device according to the present invention includes: a plurality of ultrasonic probe modules horizontally arranged in the direction of generating an ultrasonic wave; a case consisting of an outer housing with one open side for receiving and enclosing the plurality of ultrasonic probe modules, and a separation housing provided between the plurality of ultrasonic probe modules for separating the ultrasonic modules from one another, so as to detachably (Continued)

join with the ultrasonic modules; and a control module installed in the case for controlling the plurality of ultrasonic probe modules.

7 Claims, 5 Drawing Sheets

(51) Int. Cl.
  *G01N 29/22* (2006.01)
  *G10K 11/00* (2006.01)
  *G10K 11/34* (2006.01)
(52) U.S. Cl.
  CPC .......... *A61B 8/4477* (2013.01); *A61B 8/4488* (2013.01); *A61B 8/4494* (2013.01); *G01N 29/226* (2013.01); *G10K 11/004* (2013.01); *G10K 11/34* (2013.01); *G01N 2291/02475* (2013.01); *G01N 2291/106* (2013.01)
(58) Field of Classification Search
  CPC ....... A61B 8/4494; G01N 2291/02475; G01N 2291/106; G01N 29/226; G10K 11/004; G10K 11/34
  See application file for complete search history.

(56) References Cited

U.S. PATENT DOCUMENTS

| | | | |
|---|---|---|---|
| 6,045,508 | A | 4/2000 | Hossack et al. |
| 6,059,728 | A | 5/2000 | Ritter et al. |
| 6,635,019 | B2 | 10/2003 | Davidsen |
| 8,438,928 | B2 | 5/2013 | Frederick et al. |
| 2003/0055337 | A1 | 5/2003 | Lin |
| 2012/0095347 | A1 | 4/2012 | Adam et al. |

FOREIGN PATENT DOCUMENTS

| | | |
|---|---|---|
| KR | 1020100047393 A | 5/2010 |
| KR | 1020100091466 A | 8/2010 |
| KR | 1020110003056 A | 1/2011 |

OTHER PUBLICATIONS

International Search Report for PCT/KR2014/002386 dated Jun. 26, 2014.
Korean Office Action for application No. 10-2013-0052553 dated Jul. 18, 2014.
Korean Notice of Allowance for application No. 10-2013-0052553 dated Feb. 17, 2015.

DETACHABLY JOINED ULTRASONIC PROBE DEVICE

CROSS REFERENCE TO RELATED APPLICATION

This application claims the priority of Korean Patent Application No. 10-2013-0052553 filed on May 9, 2013 in the Korean Patent and Trademark Office. Further, this application is the National Phase application of International Application No. PCT/KR2014/002386 filed on Mar. 21, 2014, which is incorporated herein by reference in its entirety.

TECHNICAL FIELD

The present invention relates to an ultrasonic probe, and more particularly, a detachably joined ultrasonic probe device in which probes are modularized and various types of the probes are detachably joined and used to one ultrasonic probe apparatus

BACKGROUND ART

An ultrasonic wave is an acoustic wave having a frequency above the range of human audibility, and a sound wave having a frequency which is between about 20 kHz and 100 kHz.

Ultrasonic waves are used for inspecting inner parts of a human body or animal or for measuring, in a non-destructive manner, the thicknesses or inside combinations of solid matters such as a metal or a plastic. In these cases, ultrasonic waves are implemented in the form of a probe (hereinafter, referred to as "an ultrasonic probe") for easy handling by users.

This ultrasonic probe includes a piezoelectric ceramic to interchangeably convert an electrical signal to an acoustic signal by vibration of a piezoelectric material, an acoustic matching layer configured to decrease an acoustic impedance difference between the piezoelectric ceramic and an object so that ultrasonic waves generated in the piezoelectric ceramic can be fully delivered to the object, and a lens layer to focus ultrasonic waves propagating in a forward direction of the piezoelectric ceramic at a certain position, and a rear-side block to exclude ultrasonic waves propagating in a rearward direction of a piezoelectric layer to prevent image distortion.

Ultrasonic probes formed as these configurations have been widely used in medical field. An ultrasonic diagnosis apparatus using an ultrasonic probe applies ultrasonic waves to an organism, converts reflected ultrasonic waves to electrical signals, transmits the electrical signals to an image processing unit, and generates an image through the signals received by the image processing unit.

Through the above-described process, the ultrasonic probes have been advantageously used for detecting a foreign material in an organism, measuring the degree of injury, observing a tumor, and observing a fetus.

Since ultrasonic waves have various frequency areas, in ultrasonic diagnosis using ultrasonic probes, the range of diagnosis is limited based on the frequency areas.

Therefore, since an appropriate probe is used for a diagnosis desired by a user, there are inconveniences in that different probes should be used according to intended use.

DISCLOSURE

Technical Problem

Therefore, in a purpose of the present invention, an embodiment includes a modular ultrasonic probe and a case detachably coupled with the modular ultrasonic probe and provides a detachably joined ultrasonic probe device in which a user selects and uses an appropriate ultrasonic probe according to a performance and diagnosis frequency range which a user desires.

Technical Solution

To embody the above, one embodiment of the present invention provides a detachably joined ultrasonic probe device including a plurality of ultrasonic probe modules horizontally arranged in a direction ultrasonic wave generation, a case with an open portion in one side accommodating the plurality of ultrasonic probe modules through the open portion, an outer housing configured to enclose an exterior of the plurality of ultrasonic probe modules, and having a separation housing provided between the plurality of ultrasonic probe modules to separate each of the plurality of ultrasonic probe modules and configured to be detachably coupled with the ultrasonic probe modules, and a control module installed in the case and configured to control the plurality of ultrasonic probe modules.

In the detachably joined ultrasonic probe device according to the present invention, the ultrasonic probe module may be a linear array ultrasonic probe module in which ultrasonic waves propagate in a fixed direction or a phased array ultrasonic probe module in which the ultrasonic waves are steered and proceed in propagating according to a propagation direction and a depth.

In the detachably joined ultrasonic probe device according to the present invention, the control module may be electrically connected to the ultrasonic probe module to operate at least one of the linear array ultrasonic probe module and the phased array ultrasonic probe module.

In the detachably joined ultrasonic probe device according to the present invention, the case may accommodate the pair of phased array ultrasonic probe modules, and the linear array ultrasonic probe module disposed between the pair of phased array ultrasonic probe modules. The control module may operate the pair of the phased array ultrasonic probe module, and the linear array ultrasonic probe module to generate three dimensional image data.

In the detachably joined ultrasonic probe device according to the present invention, the ultrasonic probe device module may include a rear-side block, a piezoelectric ceramic formed on top of the rear-side block, an acoustic matching layer formed on top of the piezoelectric ceramic, an acoustic lens formed on top of the acoustic matching layer, a flexible printed circuit board disposed between the rear-side block and the piezoelectric ceramic, and a module case surrounding the rear-side block, the piezoelectric ceramic, the acoustic matching layer, the acoustic lens, and an exterior of the flexible printed circuit board excluding an upper portion of the acoustic lens, wherein the flexible printed circuit board is connected to the control module and the control module r controls the ultrasonic probe module.

In the detachably joined ultrasonic probe device according to the present invention, the ultrasonic probe module may further include a ground plate formed between the acoustic matching layer and the piezoelectric ceramic.

Advantageous Effects

A detachably joined ultrasonic probe device according to the present invention includes a modular ultrasonic probe and a case to accommodate the modular ultrasonic probe, which allows a user to select and use an appropriate ultrasonic probe based on a performance and diagnosis frequency range which a user desires so that the user uses probes of various types in one ultrasonic probe device without needing a plurality of ultrasonic probe devices.

MODES OF THE INVENTION

In the following description, only the parts necessary to understand an exemplary embodiment of the present invention will be described, the omission of descriptions of other parts is not intended to obscure the spirit of the present invention.

It should be understood that the terms used in the specification and claims set forth below are not to be construed as limited to typical or dictionary meanings, but were simply interpreted by the inventor as terms appropriately defining and explaining the invention properly on the basis of the principle that can be interpreted based on the meanings and concepts corresponding to technical aspects of the present invention. Therefore, the configurations shown in the embodiments and drawings set forth herein are merely preferable embodiments of the present invention, because they are representative of all of the technical features of the present invention, and not intended to limit the scope of the present application. In the present application it should be understood that that equivalents and modifications may be made thereto.

Hereinafter, a detachably joined ultrasonic probe device according to the present invention will be described in detail with reference to the accompanying drawings.

An ultrasonic probe is implemented in a probe shape to easily handle ultrasonic waves for inspecting inner parts of a human body or animal or for measuring, in a non-destructive manner, the thickness or inside combinations of solid matters such as a metal or a plastic.

In an ultrasonic probe, ultrasonic waves may be generated with a piezoelectric ceramic in a configuration of the ultrasonic probe, a rear-side block may absorb the ultrasonic waves which propagate toward the rear-side block, the ultrasonic waves which propagate toward an acoustic matching layer may be transferred to an object to be examined through the acoustic matching layer and an acoustic lens. This description will be described below.

Figure 1:
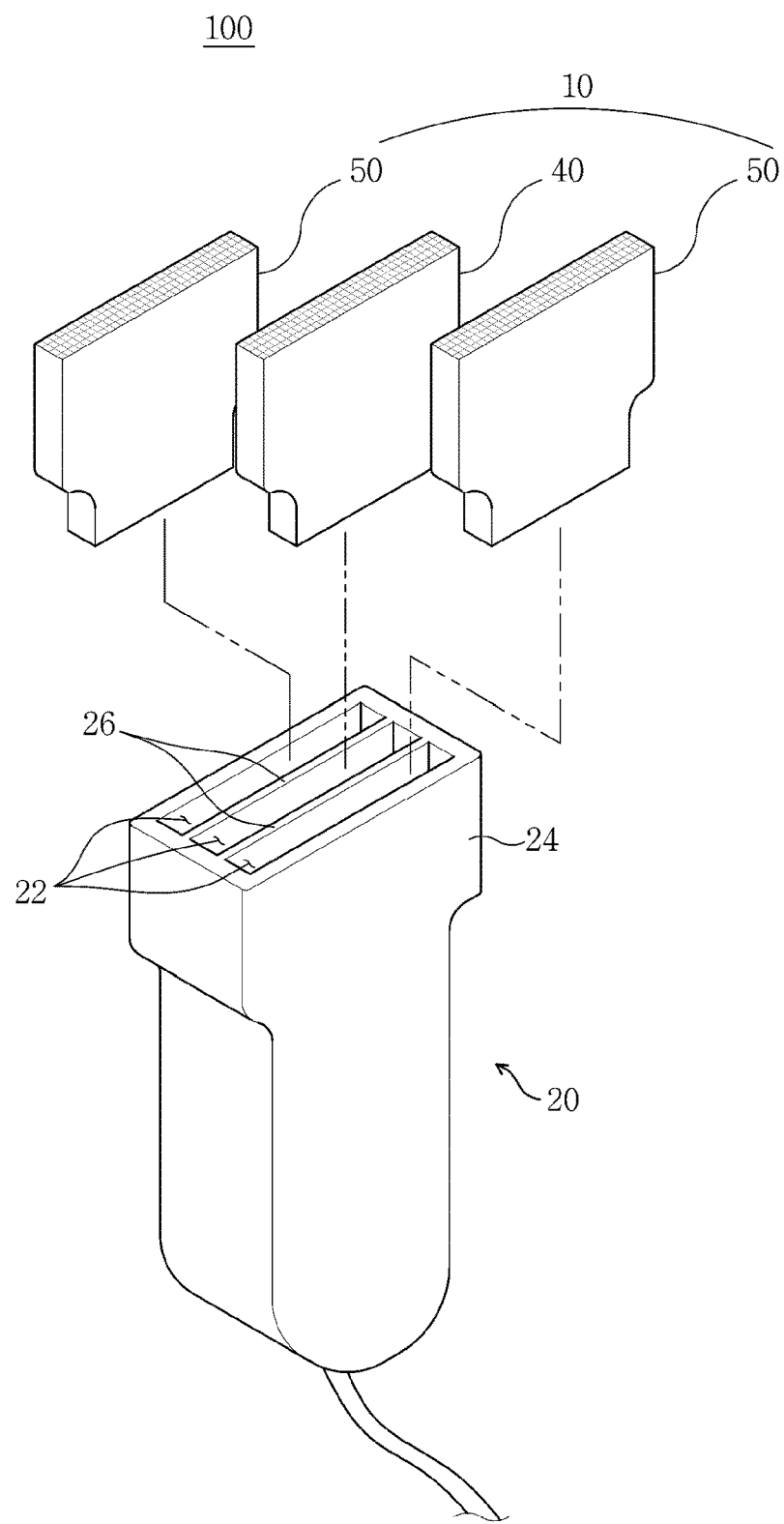
FIG. 1 is a view illustrating a configuration of a plurality of ultrasonic probe modules coupled with a case according to an embodiment of the present invention.
Figure 2:
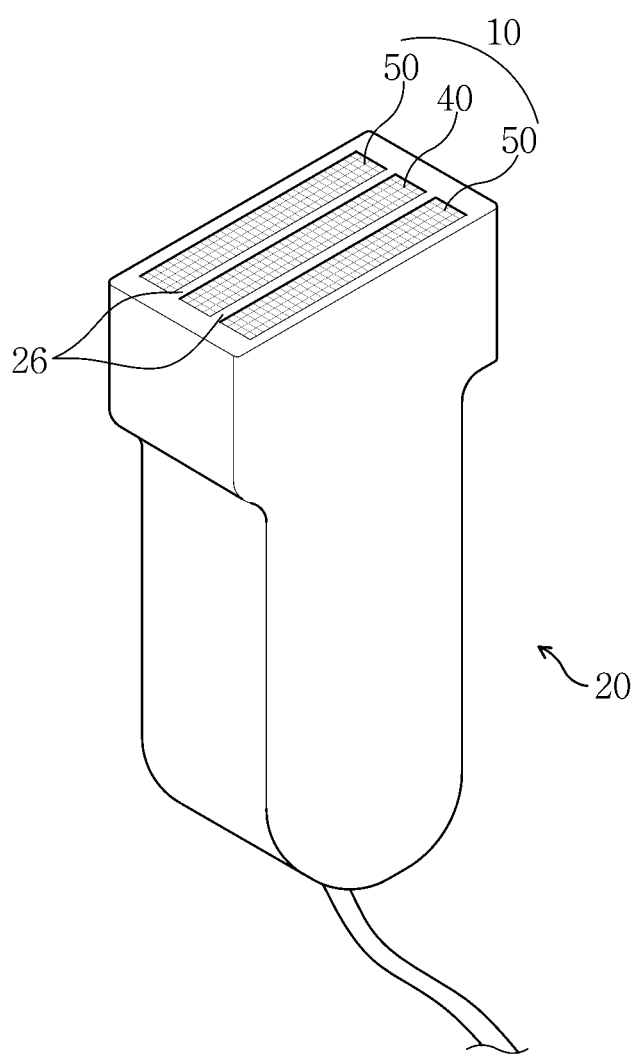
FIG. 2 is a view illustrating a detachably joined ultrasonic probe device according to the embodiment of the present invention.
Figure 3:
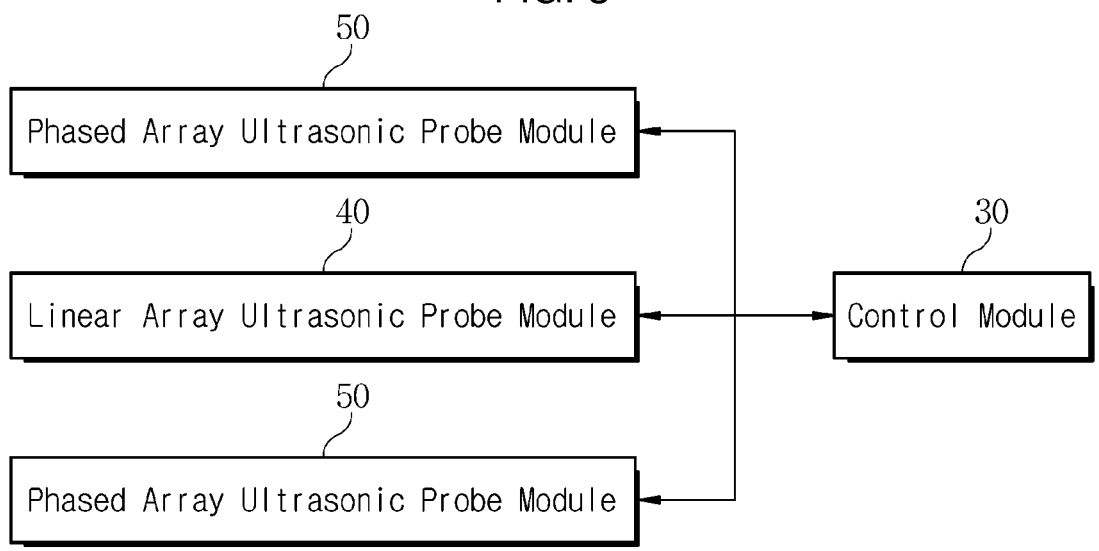
FIG. 3 is a block diagram for describing the detachably joined ultrasonic probe device according to the embodiment of the present invention.

FIG. 1 is a view illustrating a configuration of a plurality of ultrasonic probe modules coupled with a case according to one embodiment of the present invention. FIG. 2 is a view illustrating the detachably joined ultrasonic probe device according to one embodiment of the present invention. FIG. 3 is a block diagram for describing the detachably joined ultrasonic probe device according to one embodiment of the present invention.

Referring to FIGS. 1 to 3, a detachably joined ultrasonic probe device 100 according to the embodiment of the present invention includes a plurality of ultrasonic probe modules 10, a case 20 and a control module 30.

The ultrasonic probe modules 10 are modular ultrasonic probes which can be detachably coupled through open portion 22 of the case 20. That is, the ultrasonic probe modules 10 are formed for the ultrasonic probe to be accommodated and used in receiving portions formed inside the case 20 through the open portion 22 of the case 20.

The detachably joined ultrasonic probe device 100 according to one embodiment of the present invention includes the plurality of ultrasonic probe modules 10. The plurality of ultrasonic probe modules 10 is arranged in a horizontal direction with respect to a direction in which ultrasonic waves are generated and are coupled to be accommodated in the receiving portions through the open portion 22 of the case 20. The ultrasonic probe module 10 accommodated in the case 20 may be a linear array ultrasonic probe module 40 or a phased array ultrasonic probe module 50, descriptions which relate to the above modules will be described below.

The case 20 has open portion 22 formed in one side thereof, accommodates the plurality of ultrasonic probe modules 10 through the open portion 22, and includes an outer housing 24 and a separation housing 26.

The outer housing 24 encloses the exterior of the plurality of ultrasonic probe modules 10 accommodated in the open portion 22. That is, the outer housing 24 protects the plurality of ultrasonic probe modules 10 from external shocks by enclosing the exterior of the plurality of ultrasonic probe modules 10 accommodated inside the case 20.

The separation housing 26 is disposed between the plurality of ultrasonic probe modules 10 to separate each of the ultrasonic probe modules 10. That is, the separation housing 26 serves a partition role to divide the inside of the case 20 into a plurality of open portions 22, separates each of the ultrasonic probe modules 10 so that the ultrasonic probe modules 10 do not come in contact with each other and are not affected by vibrations of each other.

Materials of the case 20 may be plastic materials such as polyethylene (PE), polypropylene (PP), or polyethylene terephthalate (PET), but an aspect of the present invention is not limited thereto, and a material having a lightweight, an excellent durability, and non-conductivity may be used.

A control module 30 is installed inside the case 20 to control the plurality of ultrasonic probe modules 10. That is, the control module 30 may be electrically connected to the plurality of ultrasonic probe modules 10 which are coupled with the open portion 22 of the case 20 to operate or halt each of the ultrasonic probe modules 10.

The detachably joined ultrasonic probe device 100 according to one embodiment of the present invention may accommodate in the case 20 a pair of the phased array ultrasonic probe modules 50, and the linear array ultrasonic probe module 40 disposed between the pair of the phased array ultrasonic probe modules 50. The control module 30 is electrically connected to the pair of the phased array ultrasonic probe modules 50 and the linear array ultrasonic probe module 40 and controls each operation thereof. For example, when a user desire to use only the linear array ultrasonic probe module 40, the control module 30 halts the pair of phased array ultrasonic probe modules 50 and operates only the linear array ultrasonic probe module 40 to generate ultrasonic waves.

As described above, the ultrasonic probe module 10 according to the embodiment of the present invention may be a linear array ultrasonic probe module 40 or a phased array ultrasonic probe module 50. In connection with the above, the description made with reference to FIG. 4 is as follows.

Figure 4:
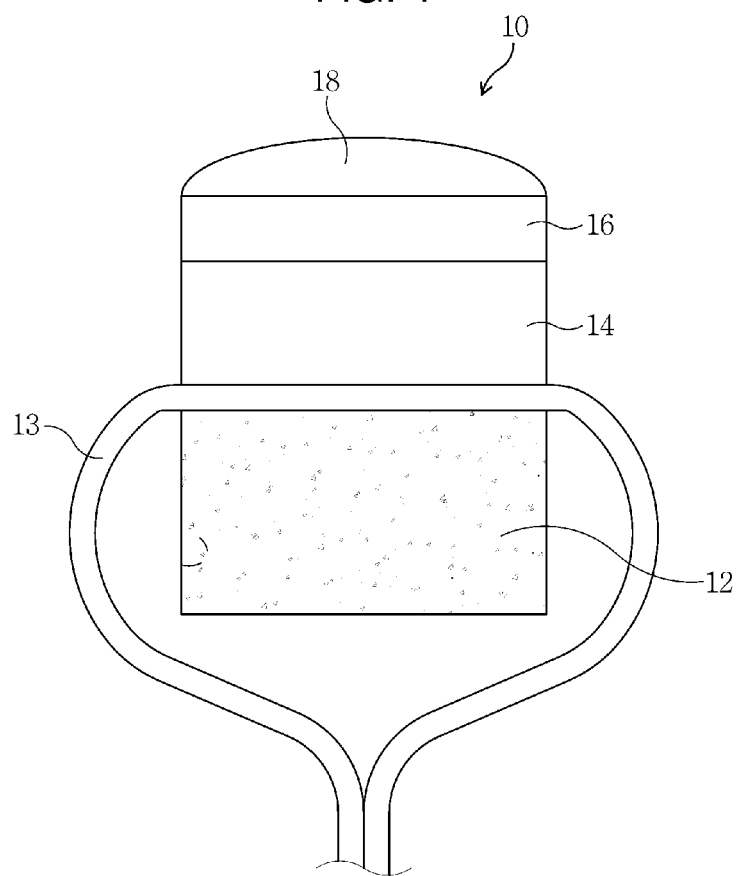
FIG. 4 is a view illustrating an ultrasonic probe module excluding a module case according to the embodiment of the present invention.

FIG. 4 is a view illustrating the ultrasonic probe module excluding a module case according to the embodiment of the present invention.

Referring to FIG. 4, the ultrasonic probe module 10 according to one embodiment of the present invention includes a rear-side block 12, a piezoelectric ceramic 14, an acoustic matching layer 16, an acoustic lens 18, a flexible circuit board 13, and the module case.

The rear-side block 12 serves to absorb ultrasonic waves among ultrasonic waves which is generated in the piezoelectric ceramic 14 and is propagating toward the rear-side block 12. An acoustic characteristic of the ultrasonic probe module 10 may be controlled through the rear-side block 12.

The piezoelectric ceramic 14 is formed on top of the rear-side block 10, converts an electrical signal into an acoustic signal to transmit it to air, and changes an ultrasonic wave reflected and returned in air back into an electrical signal again to deliver it to the device.

A ceramic material such as lead-zirconate titanate (PZT) or a single crystal material such as lead magnesium niobate-lead titanate (PMN_PT) may be used as a material of the piezoelectric ceramic 14.

The acoustic matching layer 16 may be formed on top of the piezoelectric ceramic 14, that is, on an electrode of a transceiver surface of the piezoelectric ceramic 14, to increase a reflection rate and efficiency of an ultrasonic wave. Further, the acoustic matching layer 16 may be formed to have one or more layer so as to increase the reflection rate and efficiency of an ultrasonic wave.

The acoustic lens 18 is formed on top of the acoustic matching layer 16, focuses and applies an ultrasonic wave transmitted to the object to be examined so as to increase a resolution of an ultrasonic image.

As a material of the acoustic lens 18, for example, a silicone similar to living tissue may be used.

The flexible circuit board 13 is formed between the rear-side block 12 and the piezoelectric ceramic 14 and is electrically connected to the piezoelectric ceramic 30 and the rear-side block 10. That is, interconnection patterns formed in the flexible circuit board 13 are electrically connected to electrodes formed in a rear surface of the piezoelectric ceramic 14, for example, signal electrodes, ground electrodes, and the rear-side block 12.

Furthermore, since the flexible circuit board 13 is electrically connected to the control module 30, the control module 30 may control the ultrasonic probe module 10.

The flexible circuit board 13 is electrically connected to the electrodes of the piezoelectric ceramic 14, and grounded to the rear-side block 10, and a tape circuit board of a polyimide material in which interconnection patterns are formed in the front surface may be used. Further, according to need, a tape circuit board which has both sides in which interconnection patterns are formed may be used as the flexible circuit board 13.

Since the module case encloses the exterior of the rear-side block 12, the piezoelectric ceramic 14, the acoustic matching layer 16, the acoustic lens 18 and the flexible circuit board 13 excluding the top of the acoustic lens 18, the module case protects the ultrasonic probe module 10 excluding the top of the acoustic lens 18 from external shocks.

As described above, the ultrasonic probe module 10 according to one embodiment of the present invention may be one of a linear array ultrasonic probe module 40 and a phased array ultrasonic probe module 50.

The linear array ultrasonic probe module 40 may include the piezoelectric ceramic 14 in which the ultrasonic waves propagate in a fixed direction. Here, the piezoelectric ceramic 14 is divided into a plurality of piezoelectric devices. The linear array ultrasonic probe module 40 may be used on superficial organs such as the breast, the thyroid gland, the musculoskeletal system and the like.

The phased array ultrasonic probe module 50 may steerably generate ultrasonic waves according to a propagation direction and a depth. That is, the piezoelectric ceramic 14 of the phased array ultrasonic probe module 50 may include a plurality of piezoelectric devices and each of the piezoelectric devices may generate and propagate acoustic pulses which have phase differences. In other words, the phased array ultrasonic probe module 50 may generate ultrasonic waves having phase differences by arranging every piezoelectric device in phase and steering a propagation direction of the ultrasonic waves to obtain an image. An organ such as the heart between the ribs may be tested through scanning using the phased array ultrasonic probe 90.

As described above, the detachably joined ultrasonic probe device 100 according to the embodiment of the present invention may accommodate the pair of phased array ultrasonic probe modules 50 in the case 20 and the linear array ultrasonic probe module 40 between the pair of phased array ultrasonic probe modules 50. The control module 30 may be electrically connected to and control the pair of the phased array ultrasonic probe modules 50 and the linear array ultrasonic probe module 40, respectively.

When the control module 30 operates the linear array ultrasonic probe module 40 to generate ultrasonic waves, the ultrasonic waves may be used to diagnose superficial organs such as the breast, the thyroid gland, the musculoskeletal system and the like.

When the control module 30 operates both or one of the pair of the phased array ultrasonic probe modules 50 to generate ultrasonic waves, the ultrasonic waves may be used to diagnose an organ such as the heart and/or the like through scanning. When both of the pair of phased array ultrasonic probe modules 50 are operated, ultrasonic waves may be generated to have a lower frequency than one of the pair thereof.

When the control module 30 simultaneously operates the pair of phased array ultrasonic probe modules 50 and the linear array ultrasonic probe module 40 to generate ultrasonic waves, the detachably joined ultrasonic probe device 100 according to the embodiment of the present invention may arrange each of the piezoelectric ceramics 14 in the form of a matrix array and generate a three dimensional image data.

As described above, the detachably joined ultrasonic probe device 100 according to one embodiment of the present invention may detachably couple the ultrasonic probe module 10 with the case 20 and use the ultrasonic probe module 10 having an appropriate diagnosis range and performance which a user desires.

Figure 5:
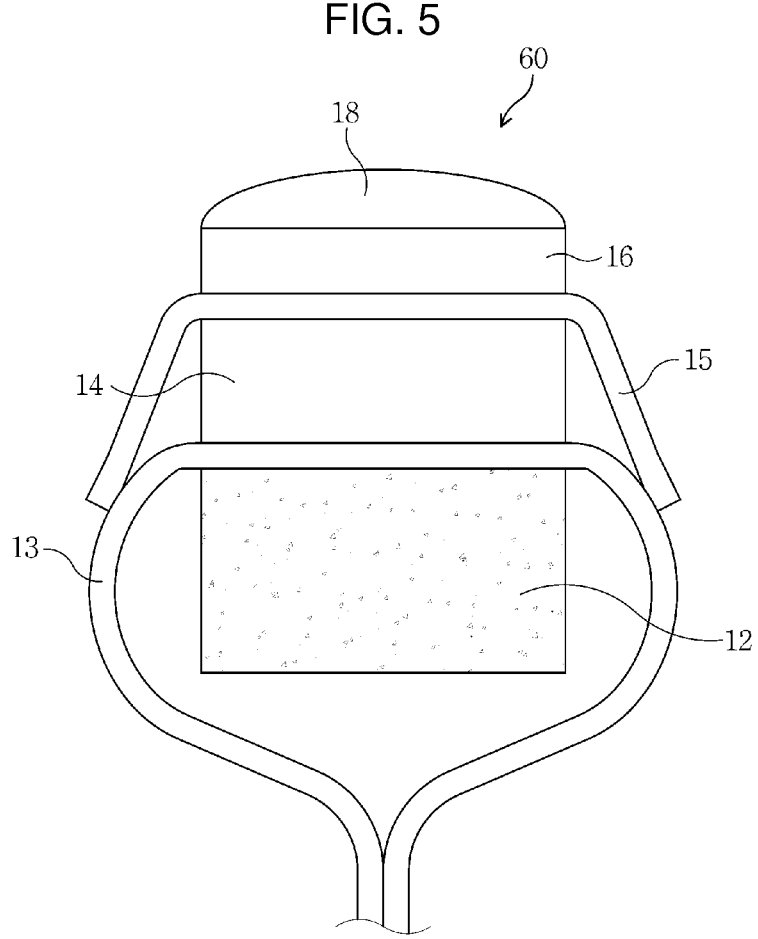
FIG. 5 is a view illustrating an ultrasonic probe module except a module case according to a second embodiment of the present invention.

As shown in FIG. 5, an ultrasonic probe module 10 according to a second embodiment of the present invention may further include a ground plate 15.

Here, FIG. 5 is a view illustrating an ultrasonic probe module excluding a module case according to the second embodiment of the present invention.

Referring to FIG. 5, since an ultrasonic probe module 60 according to the second embodiment of the present invention may have the same configuration comparatively as the ultrasonic probe module 10 in FIG. 4 except that a ground plate 15 is further provided, the following description will be focused on a structure in which the ground plate 15 is formed.

The ground plate 15 is formed between an acoustic matching layer 16 and a piezoelectric ceramic 14, and both end portions thereof are in contact with interconnection patterns of a flexible circuit board 13. That is, the ground plate 15 is in contact with the ground patterns of interconnection patterns in the flexible circuit board 13.

Since the ground plate 15 is included, the ultrasonic probe module 60 according to the second embodiment of the present invention may improve an acoustic characteristic.

On the other hand, the embodiments of the invention disclosed in the specification and drawings are merely presented as specific example for clarity and are not intended to limit the scope of the invention. It will be apparent to those of ordinary skill in the art that other modifications based on the technical concept of the present invention, in addition to the embodiments disclosed herein, can be carried out.

The invention claimed is:

1. A detachably joined ultrasonic probe device comprising:
   a plurality of ultrasonic probe modules configured to be horizontally arranged in a direction of generating an ultrasonic wave,
      wherein each ultrasonic probe module of the plurality of ultrasonic probe modules comprises a plurality of piezoelectric elements,
      wherein the plurality of ultrasonic probe modules comprise at least one first-type ultrasonic probe module and at least one second-type ultrasonic probe module, and
      wherein the at least one first-type ultrasonic probe module and the at least one second-type ultrasonic probe module are configured to target different kinds of organs;
   a case configured to accommodate the plurality of ultrasonic probe modules through an open portion formed in one side thereof and detachably couple the ultrasonic probe modules, the case including an outer housing configured to enclose an exterior of the plurality of ultrasonic probe modules and a separation housing provided between the plurality of ultrasonic probe modules to form the open portion and to separate the plurality of ultrasonic probe modules from each other such that the plurality of ultrasonic probe modules are prevented from coming in contact with each other and affecting each other by vibration thereof; and
   a controller configured to be installed inside in the case and electrically connected to the plurality of ultrasonic probe modules to selectively operate or halt each of the ultrasonic probe modules,
   wherein each of the ultrasonic probe modules includes a module case, wherein each of the module case includes a rear-side block, and each of the ultrasonic probe modules is accommodated in the open portion.

2. The device of claim 1, wherein the at least one first-type ultrasonic probe module is a linear arrayed ultrasonic probe module in which an ultrasonic wave proceed in a fixed direction, and the at least one second-type ultrasonic probe module is a phase arrayed ultrasonic probe module in which an ultrasonic wave is steered and proceeds in proportion to a proceeding direction and depth of the ultrasonic wave.

3. The device of claim 2, wherein the controller is electrically connected to both the linear arrayed ultrasonic probe module and the phase arrayed ultrasonic probe module to selectively operate at least one of the linear arrayed ultrasonic probe module and the phase arrayed ultrasonic probe module.

4. The device of claim 3, wherein the controller is further configured to simultaneously operate the phase arrayed ultrasonic probe module and the linear arrayed ultrasonic probe module to generate a three dimensional image data.

5. The device of claim 1, wherein each ultrasonic probe module of the plurality of ultrasonic probe modules includes:
   a rear-side block;
   a piezoelectric ceramic disposed on an upper portion of the rear-side block;
   an acoustic matching layer disposed on an upper portion of the piezoelectric ceramic;
   an acoustic lens disposed on an upper portion of the acoustic matching layer; and
   a flexible printed circuit board disposed between the rear-side block and the piezoelectric ceramic,
   wherein the flexible printed circuit board is connected to the controller for selectively controlling each ultrasonic probe module of the plurality of ultrasonic probe modules.

6. The device of claim 5, wherein each ultrasonic probe module of the plurality of ultrasonic probe modules further includes a ground plate formed between the acoustic matching layer and the piezoelectric ceramic.

7. An ultrasonic probe assembly comprising:
   a plurality of ultrasonic probe modules, wherein
      each ultrasonic probe module of the plurality of ultrasonic probe modules comprises a plurality of piezoelectric elements,
      the plurality of ultrasonic probe modules comprise at least one first-type ultrasonic probe module and at least one second-type ultrasonic probe module,
      the at least one first-type ultrasonic probe module and the at least one second-type ultrasonic probe module are configured to probe different kinds of targets, and
      each ultrasonic probe module of the plurality of ultrasonic probe modules is configured to be selectively operated or halted; and
   a single case, comprises:
      an open space configured to accommodate the plurality of ultrasonic probe modules;
      an outer housing; and
      a plurality of partitions,
      wherein the outer housing is configured to enclose the open space,
      wherein the plurality of partitions are configured to divide the open space into a plurality of open portions, and
      wherein each ultrasonic probe module of the plurality of ultrasonic probe modules is configured to be accommodated in each open portion of the plurality of open portions.

* * * * *